United States Patent [19]

Leighton

[11] Patent Number: 5,551,085
[45] Date of Patent: Sep. 3, 1996

[54] LOWER LUMBAR SUPPORT

[76] Inventor: Adam M. Leighton, 3138 Helix St., Spring Valley, Calif. 91977

[21] Appl. No.: 385,303

[22] Filed: Feb. 7, 1995

[51] Int. Cl.⁶ ........................................................ A61F 5/02
[52] U.S. Cl. ........................................................ 2/44; 602/19
[58] Field of Search .................................. 2/44, 45, 267, 2/310, 311, 312, 338; 450/155; 602/19

[56] References Cited

U.S. PATENT DOCUMENTS

| | | |
|---|---|---|
| 2,056,767 | 10/1936 | Blath . |
| 2,250,267 | 7/1941 | Lins . |
| 2,554,337 | 5/1951 | Lampert ................................. 602/19 |
| 2,733,712 | 2/1956 | Wuesthoff ............................. 602/19 |
| 3,554,190 | 1/1971 | Kaplan . |
| 4,080,962 | 3/1978 | Berkeley . |
| 4,099,524 | 7/1978 | Cueman et al. ....................... 602/19 |
| 4,175,553 | 11/1979 | Rosenberg . |
| 4,384,372 | 5/1983 | Rector . |
| 4,627,109 | 12/1986 | Carabelli et al. . |
| 5,086,759 | 2/1992 | Buddingh ............................. 602/19 |
| 5,399,151 | 3/1995 | Smith ..................................... 2/45 X |
| 5,437,614 | 8/1995 | Grim ..................................... 602/19 |

FOREIGN PATENT DOCUMENTS 850541 12/1939 France .

*Primary Examiner*—Jeanette E. Chapman
*Attorney, Agent, or Firm*—Brown, Martin, Haller & McClain

[57] ABSTRACT

A lower lumbar support for supporting a person's lower back muscles. The lower lumbar support includes a support belt having a first end and a second end and a belt fastener for securing the first end to the second end. The lower lumbar support also includes a first pad and a second pad, affixed to the support belt between the first and second ends, for exerting pressure on the person's lower back muscles when the lower lumbar support is being worn by said person. When the lower lumbar support is being worn, the two pads straddle the person's spine and thus lie on opposing sides of the spine. The lower lumbar support further includes a pressure strap attached to the support belt. The pressure strap has first and second wings, each of which have a tip. The tips each have a tip fastener for adjustably fastening the first and second wings to the support belt to apply further pressure to the person's lower back muscles via the pads.

11 Claims, 3 Drawing Sheets

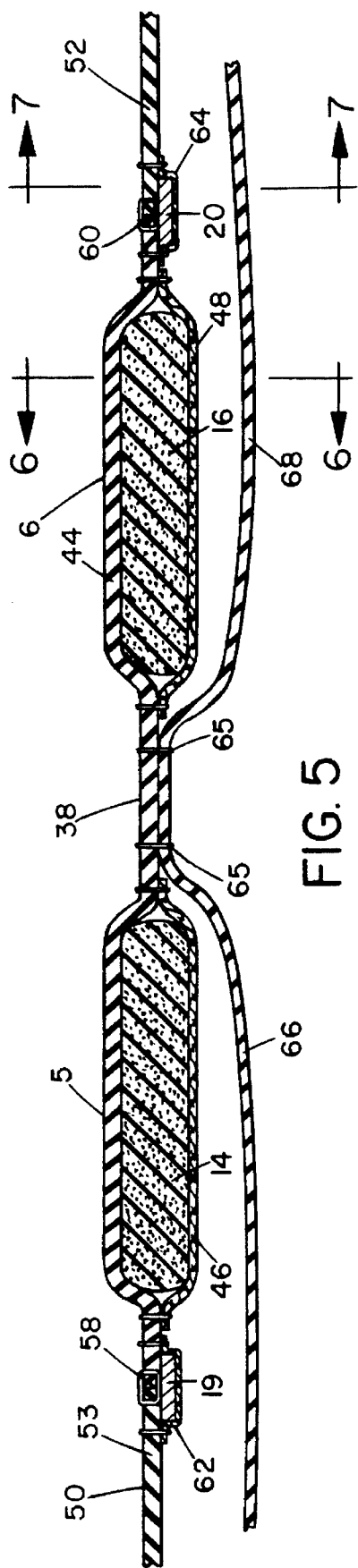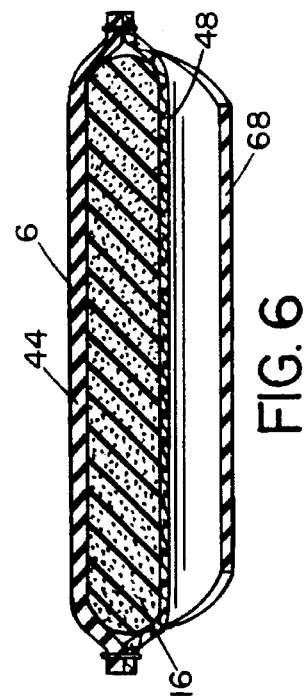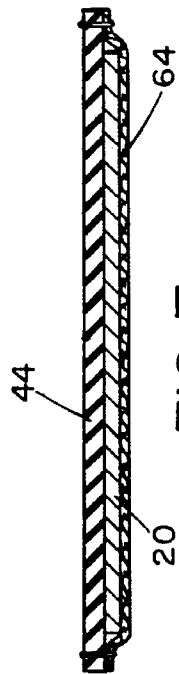

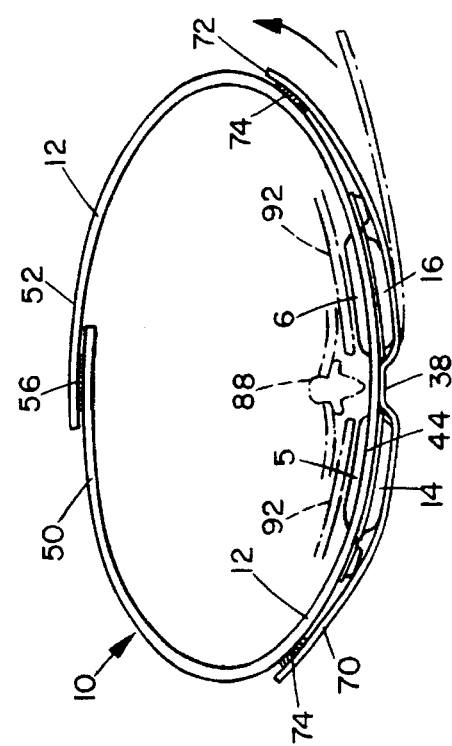
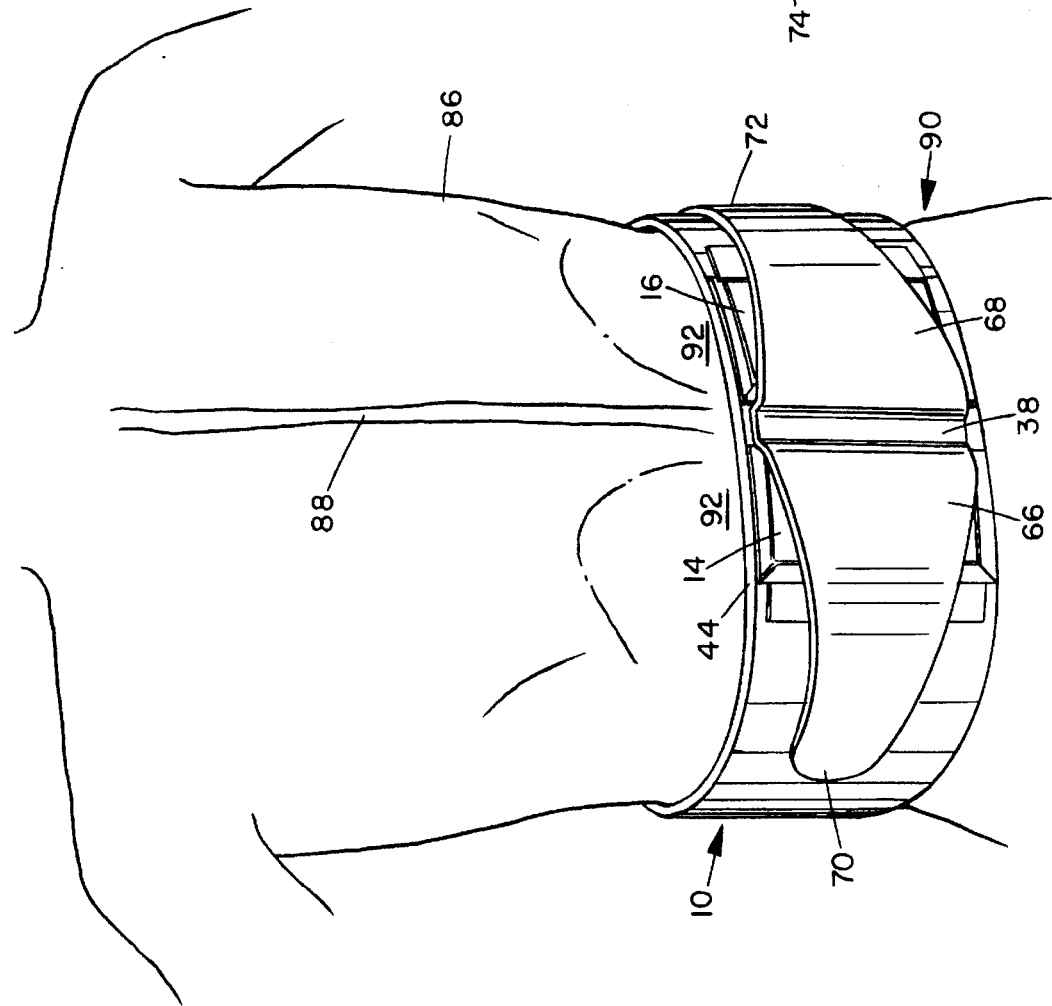
FIG. 9
FIG. 8

LOWER LUMBAR SUPPORT

BACKGROUND OF THE INVENTION

1. Field of the Invention

The present invention relates to a lower lumbar support. More particularly, the present invention relates to an apparatus and method for supporting a person's paraspinal muscle group without applying direct pressure on the person's spine.

2. Description of the Related Art

Lower back problems plague many persons. Lower back pain can range from discomforting to virtually crippling. People who suffer from lower back maladies may require everything from analgesics, to back supports, to physical therapy, to surgery.

To alleviate some of the discomfort and pain and to promote healing, lower back support devices can be extremely useful. Due to their importance in combatting lower back problems, numerous lower back support devices have been developed with varying degrees of success.

Conventional back support devices, however, suffer from a variety of drawbacks and disadvantages. For example, many such devices are bulky, heavy, and/or uncomfortable, making them impractical and difficult to use, especially for people who require portability and long periods of use. Moreover, many conventional back support devices apply pressure not only on the lower back muscles, but on the spinal column as well. Such devices, therefore, cannot equally distribute pressure on the muscle groups on both sides of the spine without also applying pressure directly on the spine. Finally, some of the recent back supports, while relatively lightweight and inexpensive, require that the wearer be sitting down with his or her back pressed against a seat to attain adequate pressure on the lower back and to thereby provide back support.

Therefore, the present invention is directed to a lower lumbar support that can apply equal pressure on the muscles on each side of the spine without pressuring the spine; that is lightweight, comfortable, easy to use, and inexpensive; and that does not require the wearer to be sitting to experience lower back muscle support.

SUMMARY OF THE INVENTION

Accordingly, the present invention is directed to an apparatus and method for providing support for a person's lower lumbar area that substantially obviates one or more of the problems due to limitations and disadvantages of the related art.

Additional features and advantages of the invention will be set forth in the description that follows, and in part will be apparent from the description, or may be learned by practice of the invention. The objectives and other advantages of the invention will be realized and attained by the apparatus and method particularly pointed out in the written description and claims hereof, as well as the appended drawings.

To achieve these and other advantages, and in accordance with the purpose of the present invention, as embodied and broadly described herein, the present invention is a lower lumbar support. The lower lumbar support comprises a belt having a first and second end, as well as a belt fastener for securing the first end to the second end. The lower lumbar support also comprises first and second pads, affixed to the belt between the first and second ends, for applying pressure to a person's lower back muscles, the pads straddling the person's spine, each of the pads lying on an opposing side of the spine when the support is being worn by the person. Finally, the lower lumbar support comprises a pressure strap attached to the belt, the pressure strap having a first and second wing, each of which has a tip, each tip having a wing fastener for adjustably fastening the first and second wings to the belt.

In another aspect, the present invention defines a lower lumbar support. The lower lumbar support comprises an elastic belt having first and second ends and having a belt fastener for adjustably securing the elastic belt around a person's torso. The lower lumbar support also comprises first and second pads affixed to the elastic belt between the first and second ends for applying pressure to the person's lower back muscles, the pads straddling the person's spine, each of the pads lying on an opposing side of the spine when the support is being worn by the person. Finally, the lower lumbar support comprises an elastic pressure strap attached to the elastic belt and over the pads, the elastic pressure strap having first and second wings, each of the wings having a tip, including a wing fastener for adjustably securing the wings to the elastic belt. When the lower lumbar support is being worn by the person and the wings are stretched and secured to the elastic belt via the wing fasteners, the pads apply pressure to the person's lower back muscles on each side of the spine.

In yet another aspect, the present invention defines a method for supporting a person's lower back. The method comprises stretching a support belt around the person's lower torso, thereby applying pressure on the person's lower back on opposing sides of the spine via first and second pads located on the support belt. The method also includes fastening the support belt around the person's lower torso. The method further comprises stretching a pressure strap around the person's lower torso and over the support belt to obtain a stretched pressure strap, thereby applying additional pressure via the pads to the person's lower back. Finally, the method comprises fastening the stretched pressure strap to the support belt.

It is to be understood that both the foregoing general description and the following detailed description are exemplary and explanatory only and are not restrictive of the invention, as claimed.

The accompanying drawings are included to provide a further understanding of the present invention. The drawings are incorporated in, and constitute a part of, this specification in order to illustrate the embodiments of the invention and, together with the description, to serve to explain the principles of the invention.

BRIEF DESCRIPTION OF THE DRAWINGS

FIG. 5 is as an enlarged sectional view taken on line 5—5 of FIG. 1.

FIG. 6 is a sectional view taken on line 6—6 of FIG. 5.

FIG. 7 is a sectional view taken on line 7—7 of FIG. 5.

FIG. 8 is a rear view of the lower lumbar support of the present invention show in use.

FIG. 9 is a top plan view of the lower lumbar support of the present invention as shown in FIG. 8.

DETAILED DESCRIPTION OF THE INVENTION

Figure 1:
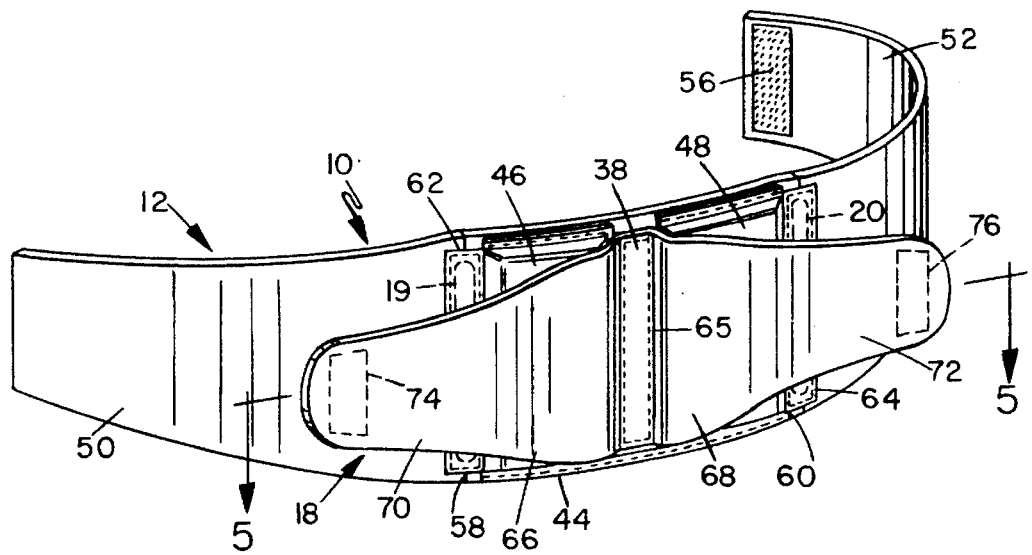
FIG. 1 is a perspective view of a preferred configuration of the lower lumbar support belt of the present invention.

Reference will now be made in detail to the present preferred embodiments of the invention, examples of which are illustrated in the accompanying drawings. Wherever possible, the same reference numerals will be used throughout the drawings to refer to the same or like parts.

In accordance with the present invention, a lower lumbar support is provided for supporting a person's lower back muscles. The lower lumbar support comprises a support belt that is fastened around the person's lower torso. The lower lumbar support includes first and second pads that are attached to the support belt, as well as a pressure strap that is preferably attached to the support belt on top of the pads. When worn around the person's lower torso, the lower lumbar support applies pressure to the lower back muscles, but not directly to the spine, providing lower back support in sitting and standing positions.

An exemplary embodiment of the lower lumbar support of the present invention is illustrated in FIG. 1 and is designated generally by reference numeral 10. As illustrated, the exemplary lower lumbar support comprises a support belt 12, cushion covers 46, 48, a pressure strap 18, and a plurality of stays 19, 20. The pressure strap 18 is attached to the support belt 12 over the cushion covers 46, 48.

In accordance with the present invention, the support belt 12 may be an elastic material that is stretched around a person's lower torso and is secured around the lower torso via a fastener 56. As embodied herein, the support belt 12 is preferably neoprene, and the fastener 56 comprises a patch of hook type fastener material such a VELCRO mounted on an end 24 of the belt 12. Herein, it is to be understood that "neoprene" comprises a wetsuit-type material, which generally includes a neoprene or rubber layer and a thinner fabric layer bonded to one or both sides of the neoprene layer to reinforce and preserve the integrity of the neoprene. Neoprene material is elastic or stretchable in all directions. When worn, the fastener 56 may be secured to the other end 26 of the belt, which is facilitated by the fact that the end 26 is neoprene. The neoprene will act as loop type fastner material that can be mated with hooks on the fastener patch 56. Alternatively, the end 26 of the belt 12 may have a complementary patch of loop-type fastener material or VELCRO® that mates with the patch 56. Preferably, the end 26 of the belt 12 will have sufficient loop-type fastener material to permit the belt 12 to be adjustably secured around the person's lower torso to attain desirable tightness of the belt 12 and hence exert pressure by pads 14, 16 on the person's lower back muscles.

Figure 3:
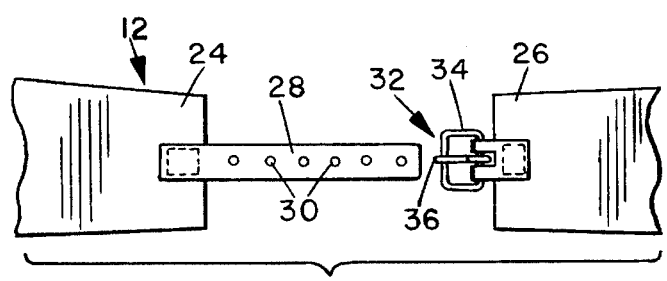
FIG. 3 illustrates an alternative fastening arrangement for the lower lumbar support of the present invention.
Figure 4:
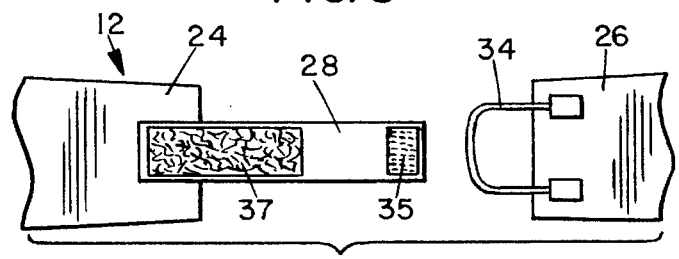
FIG. 4 illustrates a further fastening arrangement.

Alternatively, the support belt 12 may be secured around a person's Waist via a conventional belt fastener, as illustrated in FIG. 3. Therein, the end 24 of the belt 12 has a strap 28 having a plurality of holes 30. The other end 26 has a mechanism 32 including a loop 34, through which the strap 28 is passed, and a pin 36 that can be inserted through a selected one of the holes 30 to attain the desired tightness. Another alternative fastener 22 is illustrated in FIG. 4. Therein, instead of holes 30, the strap 28 may have a patch 35 of hook- or loop-type fastener material such as VEL-CRO®. When the strap 28 is passed through the loop 34 (minus the pin 36), the strap 28 is doubled over and fastened to itself via patch 37 of mating loop- or hook-type fastener material for mating engagement with patch 35. Both of the alternative fasteners illustrated in FIGS. 3 and 4 are well known to those skilled in the art.

The use of neoprene for the belt 12 enhances the beneficial therapeutic aspects of the present invention. When worn against the skin (or over clothing covering the skin), neoprene causes the body area covered by the neoprene to generate a moist heat. Here, by making at least the portion of the belt 12 covering the pads 14, 16 from neoprene, moist heat will be generated at the lower back muscles, i.e., where the pads 14, 16 contact the person's body. Moist heat aids in relaxing the back muscles and increases the blood flow, thereby increasing the therapeutic nature of the present invention. Thus, even if other portions of the belt 12 (or the lower lumbar support 10) are not made from neoprene, it is useful to make the portion of the belt covering the pads 14, 16 from neoprene. Those skilled in the art will recognize that one need not use neoprene in the present invention and that, therefore, other elastic materials may be used.

Referring now to FIGS. 1, 5, and 6, the lower lumbar support 10 of the present invention will be further described. As embodied herein and shown in FIG. 6, pads 14, 16 are provided that are mounted on the support belt 12 adjacent one another. The pads 14, 16 are secured to the support belt 12 via pad covers 46, 48. Preferably, a gap or indented channel 38 is left between the pads 14, 16 and pad covers 46, 48. The gap 38 includes a material (e.g., neoprene) interconnecting the pads 14, 16, the material in gap 38 being placed over a person's spine when the lower lumbar support 10 is being worn. In this way, when pressure is applied to the pads 14, 16, each being disposed on an opposing side of the spine and thus straddling the spine, direct pressure is applied through the pads 14, 16 on the lower back muscles, but not directly on the spine. The neoprene material in gap 38 interconnecting the pads 14, 16 thus lies over the spine.

As illustrated in FIGS. 5, 6, and 9, the pads 14, 16 may protrude from both sides of the belt 12 to form indented channels on both the inner and outer face of belt 12 between the pads. On the side of the belt 12 that lies against the person's skin, the pads 14, 16 protrude from the belt at protrusions 5, 6. Thus, as can be seen in FIG. 9, when the lower lumbar support 10 is being worn, the protrusions 5, 6 extend from the belt 12 and contact the person's lower back muscles 92 on opposing sides of the spine 88. The pads 14, 16, as interconnected by the material in gap 38, straddle the spine 88 and thus do not make contact with the spine 88. Accordingly, the pads 14, 16 do not apply direct pressure to the spine 88; only the material in gap 38 covers the spine, and that material need not (and preferably does not) make direct contact with the spine 88.

The pads 14, 16 will now be described. The pads 14, 16 may comprise rectangular shaped foam pads, approximately 7" by 4". The foam pads 14, 16 are placed within a rectangular area 44 on the support belt 12 having dimensions of 14" by 10", with the gap 38 between the pads 14, 16 being approximately 1¼" wide. The pair of pad covers 46, 48, preferably made from neoprene, are placed on top of the pads 14, 16 to attach them to the rectangular area 44. The covers 46, 48 are approximately 3 mm thick, with dimensions of 8" by 5", and are sewn onto the support belt 12 on top of the pads 14, 16.

Trapezoidal straps 50, 52 are attached to the rectangular portion 44 of the support belt 12. Alternatively, the rectangular portion 44 and the trapezoidal straps 50, 52 may be made from a single piece of neoprene. The support belt 12 is preferably made from neoprene material 53. The rectangular portion 44 and the trapezoidal straps 50, 52 are approximately 4 mm thick. Strap 52 is approximately 10" by 16½" by 6½", and strap 50 is approximately 10" by 11" by 7". Near the end 24 of the trapezoidal strap 52 is the velcro hook fastener 56 that can be fastened to the neoprene comprising the trapezoidal strap 50.

The stays 19, 20 can be placed at each joint 58, 60 between the rectangular portion 44 and the trapezoidal straps 50, 52. The stays 19, 20 are used to prevent the support belt 12 from rolling up when the lower lumbar support 10 is being worn. The stays 19, 20 may be semi-rigid or rigid and are approximately ½" thick, by 8¼" by ¾". Preferably, the stays 19, 20 are secured to the support belt 12 via fabric covers 62, 64 that are sewn onto the belt 12 over the stays 19, 20. The fabric covers 62, 64 are stronger than neoprene. Those skilled in the art will recognize that stays need not be provided and that more or fewer than two stays can be provided.

The pressure strap 18 is also attached to the support belt 12. As embodied herein, the pressure strap 18 is attached to the support belt 12 at the gap 38 between the pads 14, 16. The pressure strap 18 is preferably made from neoprene fabric and is sewn onto the belt 12 at the neoprene material in gap 38 via stitching 65, as shown in FIGS. 1 and 5. The pressure strap 18 has two wings 66, 68 that cover the pads 14, 16 and the pad covers 46, 48 when the pressure strap 18 is attached to the belt 12. At the tips 70, 72 of the wings 66, 68 are fasteners 74, 76, preferably patches of hook-type fastener material such as VELCRO®. When the support belt 12 is secured around a person's lower torso, the tips 70, 72 of the wings 66, 68 are pulled, and the fasteners 74, 76 are secured to the belt 12 over the person's right and left sides. This is illustrated in FIGS. 8 and 9. Of course, the point at which the fasteners 74, 76 are secured to the belt 12 depends on the desired pressure on the back muscles via the pads 14, 16 and thus how much the wings 66, 68 are stretched. The wings 66, 68 each cover one of the pads 14, 16, thereby applying equal (or unequal) pressure against the person's lower back muscles. Depending on the amount each wing 66, 68 is pulled and stretched around the person's lower torso, pressure can be independently increased and decreased on the pads 14, 16. It will be understood that the pressure applied by each stretched wing to the underlying pad will be uniform over the area of the pad, and that the pad will therefore apply uniform pressure to the underlying muscles.

Cross sections of the lower lumbar support 10 of the present invention are shown in FIGS. 6 and 7. FIG. 6 is a cross section taken along pad 16, illustrating the pad 16 secured to the rectangular portion 44 of the belt 12 by pad cover 48. Wing 68 covers pad 16 and pad cover 48. FIG. 7 is a cross section taken along stay 20, illustrating the stay 20 secured to the rectangular portion 44 by the fabric cover 64.

Figure 2:
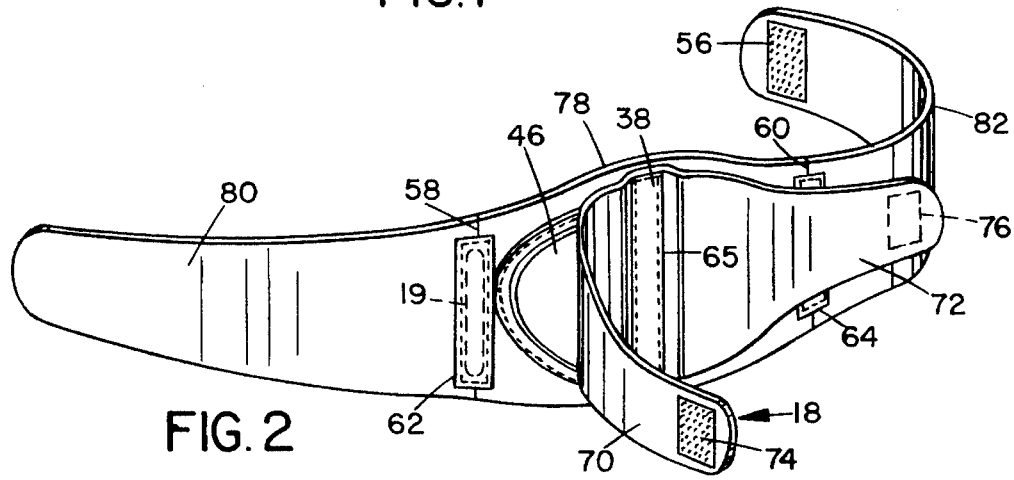
FIG. 2 is a perspective view of an alternative, lighter configuration of the lower lumbar support belt.

Referring now to FIG. 2, a second embodiment of the lower lumbar support 10 of the present invention will be described. This second embodiment, having smaller dimensions than that previously described, is better suited for women, while the first embodiment illustrated in FIG. 1 better suits men. In this second embodiment, the pads 14, 16 are preferably generally of D-shaped outer periphery, with a straight edge adjacent channel 38 and a rounded edge projecting away from channel 38, as illustrated in FIG. 2. This shape has been found to conform more readily to the body contours of individuals with slim body frames. The pad dimensions are approximately 7¼" by 4" by 5" by ½" thick. As in the first embodiment, the pads 14, 16 are secured to the support belt 12 by pad covers 46, 48 (the latter cover 48 not being shown in FIG. 2), both of which covers are preferably neoprene and approximately 8" by 5" by 6". The pads 14, 16 are attached to patch 78, which is attached to a pair of substantially rectangular straps 80, 82. The patch 78 is approximately 14" by 9", and the straps 80, 82 are approximately 14" by 3" by 5".

Strap 82 is supplied with a fastener (or patch of hook-type fastener material such as VELCRO®) 56 for securing strap 82 to strap 80 around a person's lower torso. As with the first embodiment illustrated in FIG. 1, if the support belt 12 is elastic, the straps 80, 82 are stretched around the person's lower torso and secured to each other by the fastener 56, thereby generating pressure on the person's lower back muscles via the pads 14, 16. Preferably, as described above, rigid or semi-rigid stays 19, 20 are provided on either side of the pads 14, 16 at the joints 58, 60 between the patch 78 and the straps 80, 82. The stays 19, 20, are disposed substantially parallel to the person's spine when the lumbar support 10 is being worn. In this second embodiment, the stays 19, 20, are approximately 4" long and less than 1" wide. They are covered and attached to the support belt 12 with covers 62, 64 that are approximately 1" by 5". The covers may be neoprene, but are preferably a fabric that is stronger than neoprene.

In the second embodiment, the pressure strap 18 may have an "eye" shape, as illustrated in FIG. 2. As embodied herein, the pressure strap 18 is preferably sewn onto the support belt 12 at point 38 via stitching 65 between the pad covers 46, 48. As described above, the pressure strap 18 has a pair of wings having tips 70, 72, each tip 70, 72 having a tip fastener 74, 76 for securing the wing tips 70, 72 to the straps 80, 82. The fasteners 74, 76 can be patches of hook-type fastener material such as VELCRO® that attach directly to the straps 80, 82, if the straps are made of neoprene. If not neoprene, the straps 80, 82 may have a patch of mating loop-type VELCRO along their length for mating to the fasteners 74, 76 of hook type fastner material. As above, the pressure strap 18 is placed over the pads 14, 16 and is used to increase and decrease the pressure applied on the lower back muscles by the pads 14, 16 by pulling and stretching the wings of the pressure strap 18 around the person's lower torso and fastening them to the straps 80, 82. The pressure strap 18, in the second embodiment, is approximately 22" by 3" at the tips 70, 72, and 8½" high at the attachment point.

With reference to FIGS. 8 and 9, when a person 86 uses either of the above described embodiments of the lumbar support 10 of the present invention, lower back support can be attained without directly pressuring the spine 88 and without the need to sit in a chair with the person's back against the back of the chair. The trapezoidal straps 50, 52 of the support belt 12 are stretched and fastened about the person's lower torso 90 via the fastener 56, thereby applying direct pressure to the person's lower back muscles 92 via the pads 14, 16. The belt 12 can be stretched as much or as little as necessary to attain the desired pressure. Because the pads 14, 16, as interconnected by the material in gap 38, straddle the spine 88, direct pressure is not applied by the pads 14, 16 to the spine 88.

With the belt 12 fastened, the person 86 wearing the lumbar support 10 can pull and stretch the wings 66, 68 of the pressure strap 18 about the lower torso 90, thereby increasing pressure on the pads 14, 16 and, in turn, increasing pressure on the lower back muscles 92. The wings 66, 68 can be independently stretched to apply as much or as little pressure on the lower back muscles 92. The wings 66, 68 are then fastened to the belt 12 via the fasteners 74, 76 on the wing tips 70, 72. If the person 86 wearing the lumbar support 10 is experiencing too much pressure on the back muscles 92, the wings 66, 68 can be unfastened from the support belt 12 and then refastened to the support belt 12, with the wings 66, 68 being less stretched around the torso 90.

It will be apparent to those skilled in the art that various modifications and variations can be made in the apparatus and method of the present invention without departing from the spirit or scope of the invention. Thus, it is intended that the present invention cover the modifications and variations of this invention, provided they come within the scope of the appended claims and their equivalents.

What is claimed is:

1. A support belt, comprising:

a first elongate strap member of elastic material having opposite first and second ends and a fastener for securing the strap member around a person's lower torso, the strap member having an outer face and an inner face and defining a central plane;

the first strap member having a narrow, inwardly facing channel for overlying a wearer's spine when the member is secured around the wearer's lower torso;

a first pad and a second pad secured to the strap member on opposite sides of the channel so as to extend up to opposite side edges of said channel, whereby said pads are positioned on opposite sides closely adjacent a wearer's spine but do not overlie the spine;

each pad projecting inwardly through the central plane defined by said strap member to form projecting regions on the inner face of the strap member and defining opposite side walls of said channel, whereby said strap member is spaced away from a wearer's spine at said channel and does not press against a wearer's spine, and said pads comprise means for exerting pressure on a wearer's lower back muscles; and first and second wing strap portions of elastic material attached to the outer surface of said strap member between said pads, each wing strap portion having an outer free end and a fastener at the outer end of each wing strap portion for adjustable connection to an underlying portion of the strap member, the first and second wing strap portion comprising means for stretching over the first and second pads, respectively, and biasing said pads inwardly to apply a selected amount of pressure to the underlying muscles when said wing strap portions are secured to respective underlying portions of said strap member, whereby stretching each wing strap portion away from said channel in opposite directions acts to pull said channel outwardly away from the wearer's spine.

2. The belt as claimed in claim 1, wherein said pads are secured to the outer surface of the strap member and bias overlying portions of said strap material inwardly to form said channel overlying a wearer's spine.

3. The belt as claimed in claim 2, wherein said pads are of flexible foam material.

4. The belt as claimed in claim 2, wherein said pads are each of rectangular shape.

5. The belt as claimed in claim 2, wherein the pads each have a D-shaped outer periphery and have a straight edge adjacent said channel and a rounded edge projecting away from said channel.

6. The belt as claimed in claim 2, wherein said pads form protrusions on both the inner and outer face of said strap member.

7. The belt as claimed in claim 2, including a piece of material covering each pad on the outer face of said strap member.

8. The belt as claimed in claim 1, wherein the material of said strap member and said wing strap portions is stretchable in all directions.

9. The belt as claimed in claim 8, wherein said strap member is of neoprene material, and said pads are secured on the outer face of said strap member, whereby portions of said neoprene material overlying said pads are urged inwardly by said pads against a wearer's back muscle regions to generate a moist heat while the belt is worn.

10. The belt as claimed in claim 9, wherein said neoprene material has an outer fabric layer of loop-type fastener material, and the fastener of each wing strap portion comprises a patch of hook-type fastener material for releasable mating engagement with said loop-type fastener material at any selected position on said strap member.

11. A support belt, comprising:

an elongate belt member of elastic material, the belt member defining a belt plane and having opposite ends, an inner face, and an outer face;

fastener means at opposite ends of said belt member for securing said belt member around a wearer's torso in the lower lumbar region;

first and second cushion pads secured to the outer face of the belt member and projecting inwardly across the belt plane to form protrusions on both the inner and outer face of the belt;

the cushion pads being spaced apart to define a narrow, indented channel between the pads at a predetermined position on the belt member for overlying a wearer's spine when the belt is worn, whereby said pads are positioned closely adjacent a wearer's spine but do not apply pressure to the spine;

first and second wing straps each having a first end secured to the belt member between the cushion pads and a second, free end, the second end of each wing strap having fastener means for securing the wing strap to a selected underlying portion of the outer face of said belt member; and said wing straps comprising means for stretching over the outer pad protrusions on opposite sides of said channel and biasing the respective pads inwardly to apply pressure to a wearer's lower back muscles, said belt member outer face having mating fastener means extending lengthwise along said belt for releasable engagement with said wing strap fastener means, whereby each wing strap fastener means is securable to said belt at any selected position on said mating fastener means to adjust the pressure applied to the underlying back muscles, wherein each pad applies a uniform pressure over the area of said pad.

* * * * *